(12) United States Patent
Alvarado

(10) Patent No.: US 7,727,138 B2
(45) Date of Patent: Jun. 1, 2010

(54) MAGNETIC APPARATUS FOR THE TREATMENT OF CATARACTS AND OTHER EYE CONDITIONS

(76) Inventor: Alfredo Alvarado, 2711 Kinsington Cr., Weston, FL (US) 33332

( * ) Notice: Subject to any disclaimer, the term of this patent is extended or adjusted under 35 U.S.C. 154(b) by 1007 days.

(21) Appl. No.: 11/176,516

(22) Filed: Jul. 7, 2005

(65) Prior Publication Data

US 2007/0073096 A1   Mar. 29, 2007

(51) Int. Cl.
*A61N 2/00* (2006.01)
(52) U.S. Cl. .......................................... 600/9; 351/158
(58) Field of Classification Search .................. 600/9; 351/167, 45–46, 112, 133, 230, 158; 2/12–13, 2/431, 434, 445; 128/898–899
See application file for complete search history.

(56) References Cited

U.S. PATENT DOCUMENTS

| | | | | |
|---|---|---|---|---|
| 4,070,103 A | * | 1/1978 | Meeker | ........................ 351/52 |
| 4,582,401 A | * | 4/1986 | Grindle | ........................ 351/45 |
| 4,786,159 A | * | 11/1988 | Piazza et al. | ................. 351/132 |
| 5,085,627 A | | 2/1992 | Fedorov et al. | |
| 5,096,284 A | | 3/1992 | NakaMats | |
| 5,106,178 A | * | 4/1992 | Akiyoshi | ..................... 351/57 |
| 5,120,119 A | | 6/1992 | Mats | |
| 5,135,466 A | | 8/1992 | Fedorov et al. | |
| 5,181,051 A | | 1/1993 | Townsend et al. | |
| 5,269,746 A | | 12/1993 | Jacobson | |
| 5,389,981 A | | 2/1995 | Riach, Jr. | |
| 6,015,377 A | * | 1/2000 | Brown et al. | .................... 600/9 |
| 6,050,931 A | * | 4/2000 | Russell | ......................... 600/15 |
| 6,053,859 A | | 4/2000 | Haglund | |
| 6,093,143 A | * | 7/2000 | Nagler | ......................... 600/15 |
| 6,126,588 A | | 10/2000 | Flamant et al. | |
| 6,186,332 B1 | * | 2/2001 | Combs | ........................ 206/759 |
| 6,344,021 B1 | * | 2/2002 | Juster et al. | .................... 600/15 |
| 6,368,293 B1 | * | 4/2002 | Orgeron et al. | ................ 601/15 |
| 6,406,419 B1 | | 6/2002 | Farahmand | |
| 6,610,023 B2 | | 8/2003 | Steponovich | |
| 6,637,484 B1 | * | 10/2003 | Kraft | ........................... 150/112 |
| 6,841,393 B2 | | 1/2005 | Koenig | |
| 2003/0056281 A1 | * | 3/2003 | Hasegawa | ....................... 2/428 |

* cited by examiner

*Primary Examiner*—John P Lacyk
(74) *Attorney, Agent, or Firm*—Mark D. Bowen, Esq.; Malin Haley DiMaggio Bowen & Lhota, P.A.

(57) ABSTRACT

An apparatus for magnetic therapy of eye conditions such as cataracts, eye floaters, chronic glaucoma, age-related maculopathy, diabetic retinopathy, dry eyes, watery eyes and myopia is disclosed. The apparatus comprises a combination of two bi-polar magnets enclosed in a supportive cover that saddles the upper rim of regular eyeglasses. The magnets are placed in a proper position in front of the affected eye and their polarity can be changed at any time without any difficulty. The magnets are preferably solid discs of Neodymium-Iron-Boron (NdFeB) with a surface strength of 1300 to 1800 gauss.

5 Claims, 2 Drawing Sheets

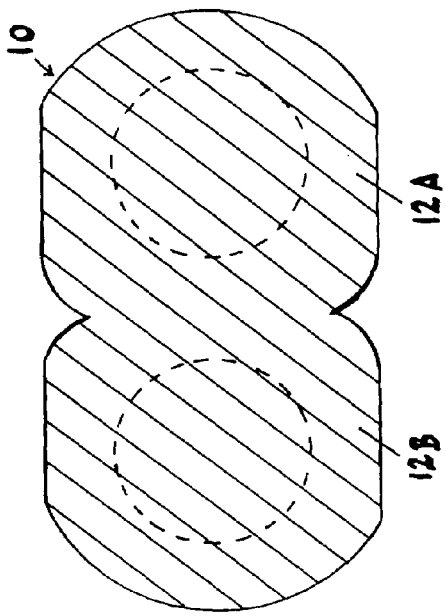
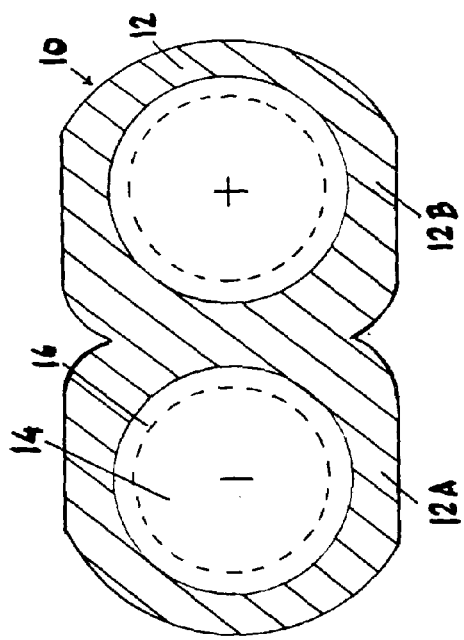
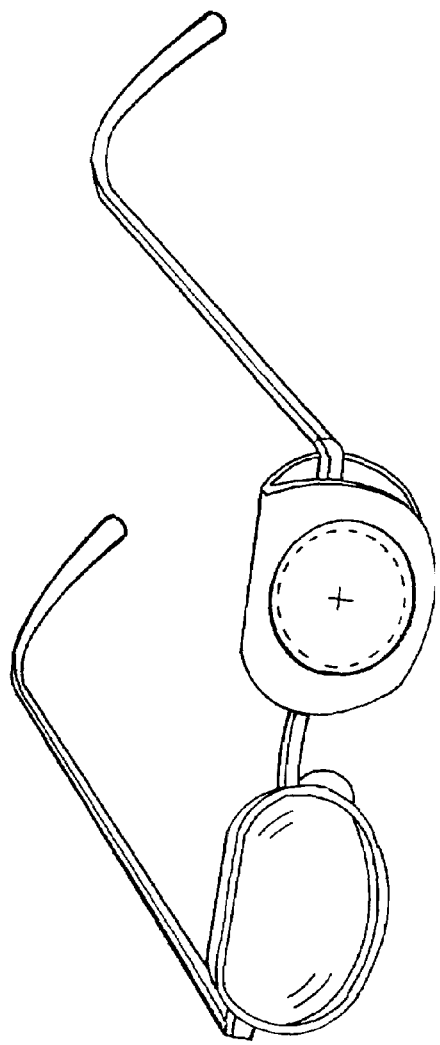

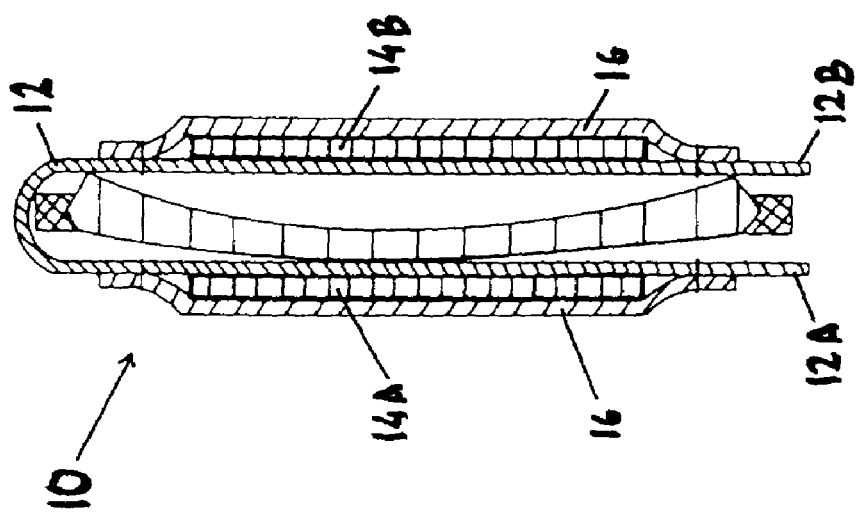

MAGNETIC APPARATUS FOR THE TREATMENT OF CATARACTS AND OTHER EYE CONDITIONS

CROSS REFERENCE TO RELATED APPLICATIONS

N/A

STATEMENT REGARDING FEDERALLY SPONSORED RESEARCH OR DEVELOPMENT

N/A

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office patent file or records, but otherwise reserves all copyrights rights whatsoever.

BACKGROUND OF THE INVENTION

1. Field of the Invention

The present invention is related to a simple magnetic apparatus for the treatment of cataracts and other eye conditions.

2. Description of Related Art

Cataract is the leading cause of blindness in the world today, while age-related macular degeneration is responsible for the majority of new cases of visual impairment in the western world. It is estimated that in 2004, 1.75 million U.S. residents have significant symptoms associated with age-related macular degeneration. The challenge is awesome: More than 160 million people have visual impairment, with three quarters of the cases related to cataract and two thirds of them avoidable. Sixty percent of world blindness occurs in China, India and Sub-Saharan Africa; blindness numbers are estimated to be increasing at the rate of more than 2 million cases annually; and as the population ages, the number of people older than 45 years is expected to double by the year 2020.

Cataract is treated with surgery because no other medical treatment has been found to prevent or to reverse senile cataract. However cataract surgery involve certain risks. Park and Kim reporting on 35 eyes of 35 patients they found that tear occurred during phacoemulsification in 51.4% of cases, during irrigation and aspiration in 34.4%, and during capsulorrhexis or lens implantation in the remainder. After the tear had occurred, careful and adequate vitrectomy, attention to lens positioning and anterior chamber reconstruction allowed a final vision of 0.8 or better in 60% of eyes, and 0.5% or better in 77.1%.

Furthermore cataract surgery increases the risk for late age-related maculopathy (ARM). The Beaver Dam eye study found an association of cataract and subsequent risk for early ARM.

Nevertheless surgical removal remains the standard treatment for cataract now and in the foreseeable future. Cataract surgery is the most frequently performed surgery in the United States, with over 1.5 million cataract surgeries done each year. Nine out of 10 people who have cataract surgery regain very good vision, somewhere between 20/20 and 20/40. The worldwide burden of this problem is immense. While results for the treatment of cataracts are excellent today, improvements in safety and refraction precision are needed. Other approaches are desperately needed to stem the worldwide tide of cataract related ocular dysfunction.

Alternative approaches to the treatment of cataracts exist. Among the alternative approaches is the use of magnetic therapy. Magnetic therapy is the application of magnetic fields on parts of the body to speed healing, relieve pain and inflammation, and improve bodily function. Possible beneficial effects on blood flow in and around the optic nerve head and on direct protection of retinal ganglion cells, so-called neuroprotection, may be attained by the use of magnetotherapy.

In recent times, the biological effects of magnetic fields have been studied in Japan, the Soviet Union, Europe and the United States. Most of the Japanese products used in magnetic therapy are bipolar in the sense that when they are used, they apply both North and South pole magnetic energies to the body. Numerous theories and hypothesis have been proposed to explain the observed effects, but at this time there is still no single explanation, which is accepted as definitive.

A U.S. researcher, Albert Roy Davis, is credited with the discovery of that the two poles of a magnet have different and essentially opposite effects on both living and non-living systems, and contrary to the action of most of the Japanese devices, the energy from essentially one pole or other is used. These polar effects are deemed monopolar for one pole. The poles spin in opposite directions and have opposite properties. Specifically North Pole energies rotate in a counter-clockwise direction and have been found to cause mass to contract and condense. On the other hand, South Pole energies rotate in a clockwise direction and cause mass to expand and dissipate.

McLaughlan at Oxford University reported effects by very weak magnetic fields on chemical reactions and suggests that they are influencing the spin state of electrons in such a way to slow down their reaction.

History of Magnetotherapy

The history of magnetism goes back to many centuries before Christ. The earliest mention of the magnet as a healing agent is one of the four Vedas on the treatise of medicine, the Atharveda. The ancient Egyptians were also apparently familiar with the properties of magnetic forces as they utilized them to preserve mummies. Their legendary beauty, Cleopatra, was said to have worn a tiny magnet on her forehead, probably to preserve her charms. Most civilizations, however, invested the magnet with magical powers. They wore magnets as amulets or charms to relieve aches and pains, its healing properties were used unwittingly.

Centuries before Christ the Greeks knew that the mineral magnetite attracts iron. Lucretius mentioned that "iron can be drawn by that stone which the Greeks call magnet by its native name because it has its origins in the hereditary bounds of the Magnetes" the inhabitants of Magnesia, in Thessaly. The romans knew also that magnetism can act to repel: "sometimes, too, iron draws back from this stone; for it is wont to flee from and follow it in turn."

Nature of Magnetism

The behavior of ferromagnetics is one of the hardest phenomena to explain in terms of conventional physics. A ferromagnetic substance has been long regarded as an assemblage of small magnets, each magnet a group of atoms. When the material is un-magnetized the groups are arranged with haphazard orientations; when it is magnetized they are lined up with their axes approximately parallel. The nature of this small magnet, or domain, has been the subject of much consideration over a period of years, and now it is known that all ferromagnetic materials are composed of such domains, each of which consists of many atoms. Within a domain the atomic moments are aligned parallel to each other, even when no field is applied, and they are therefore said to be spontaneously magnetized.

The ultimate magnetic particle is the spinning electron, and a change in magnetization fundamentally results from a change in the directions of spin of certain electrons, and to a secondary extent from a change in their orbital motions. In iron, cobalt and nickel the electrons responsible for ferromagnetism lie in the incomplete third atomic shell; in the rare earths, like neodymium, they are in the fourth shell.

Magnets have two poles, a north pole and a south pole. However, these must not be confused with the earth's geographic north and south poles, so a magnet's north seeking pole is really its south pole and a magnet's south looking pole is really its north pole. The negative/north pole calms the body, neutralizes pH and increases oxygen and reduces cellular swelling, while the positive/south pole stresses the body, increases acidity, reduces oxygen and increase cellular swelling. Some doctors prefer only north pole, whereas others prefer south pole for treatment.

In 1983, one of the greatest discoveries ever in magnetism was announced. Rare earth Neodymium-Iron-Boron (NdFeB) magnets were invented which are 700% as powerful as the older ceramic magnets. The neodymium biomagnets hold their charge indefinitely, with no significant loss of power after 10 years. The traditional magnets were often about only 300-400 surface gauss, but the new neodymium biomagnets are as much as 2500 surface gauss. In comparison, refrigerator magnets are about 10 gauss, and the earth's magnetic field is 0.5 gauss only. Magnet's potency varies from high to low potency. High potency magnets have 4000 gauss, moderate potency magnets range between 1500 and 2500 gauss, and low potency fluctuates between 200 and 800 gauss. Magnetotherapy acts through three established physical mechanisms: Magnetic induction, magnetomechanical effects and electronic interactions.

There is another form of magnetic therapy, the so-called pulsed magnetic field, that requires expensive electronic equipment and is used under the supervision of a physician. An example of this is a rotating magnetic field as described by Fedorov in the U.S. Pat. No. 5,085,627 for the treatment of diseases of the optic tract such as maculodystrophy, retrobulbar neuritis, and partial atrophy of the optic nerve. However this method may produce some disagreeable sensations, such as headache and a sense of pressure in the areas of the eyeball.

Advantages of Magnetic Therapy

1. Permanent magnets constitutes an entirely painless method for treatment of cataracts and other eye conditions.

2. Permanent magnets are exceptionally safe, they have no known side effects and can be used as often as necessary.

3. They can be used at home by the same patient following simple instructions.

4. Magnets are affordable.

5. Magnets are durable, are fully charged with electromagnetic current and remain permanently magnetized.

6. Magnetism affects every cell and tissue of the body.

Accordingly, there exists a need for an apparatus for magnetic therapy of eye conditions such as cataracts, eye floaters, chronic glaucoma, age-related maculopathy, diabetic retinopathy, dry eyes, watery eyes and myopia.

BRIEF SUMMARY OF THE INVENTION

The present invention relates to an apparatus for magnetic therapy of eye conditions such as cataracts, eye floaters, chronic glaucoma, age-related maculopathy, diabetic retinopathy, dry eyes, watery eyes and myopia. In accordance with a preferred embodiment, a apparatus in accordance with the present invention comprises a combination of two bi-polar magnets enclosed in a supportive cover that saddles the upper rim of regular eyeglasses. The magnets are placed in a proper position in front of the affected eye and their polarity can be changed at any time without any difficulty. The magnets are preferably solid discs of Neodymium-Iron-Boron (NdFeB) with a surface strength of 1300 to 1800 gauss.

Accordingly, it is an object of the present invention to provide improvements in the field of magnet therapy.

Another object of the present invention is to provide a simple magnetic apparatus for the treatment of cataracts and other eye conditions.

Still another object of the present invention is to provide a magnetic apparatus that keeps the magnets under control, avoiding jumping toward each other.

Yet another object of the present invention is to provide a magnetic apparatus that is user friendly, and can be mounted without any difficulty.

Another object of the present invention is to provide a magnetic apparatus wherein the polarity of the device can be changed very easily, as needed.

Still another object of the present invention is to provide a magnetic apparatus that can be used at any time at leisure at home.

Yet another object of the present invention is to provide a magnetic apparatus made of a semirigid thin plastic material that will not scratch the eyeglasses lens.

In accordance with these and other objects, which will become apparent hereinafter, the instant invention will now be described with particular reference to the accompanying drawings.

BRIEF DESCRIPTION OF THE SEVERAL VIEWS OF THE DRAWINGS

FIG. 1 depicts a first side of a magnetic apparatus for the treatment of cataracts and other eye conditions in accordance with the present invention in an open configuration;

FIG. 2 depicts the second side thereof;

FIG. 3 illustrates the magnetic apparatus installed on a pair of conventional eye glasses; and FIG. 4 is a side sectional view of the magnetic apparatus in the installed configuration.

DETAILED DESCRIPTION OF THE INVENTION

With reference now to the drawings, FIGS. 1-4 depict a preferred embodiment of a magnetic apparatus, generally referenced as 10, in accordance with the present invention. Magnetic apparatus 10 provides an apparatus for magnetic therapy of eye conditions such as cataracts, eye floaters, chronic glaucoma, age-related maculopathy, diabetic retinopathy, dry eyes, watery eyes and myopia. Apparatus 10 comprises a foldable main body 12 sized for sandwiched installation over a lens on a pair of glasses as best illustrated in FIGS. 3 and 4.

Main body 12 includes adjacent side portions, referenced as 12A and 12B, each of which is generally sized for covering relation with a lens on a pair of conventional glasses. Each side portion 12A and 12B is adapted with a bi-polar magnet, referenced as 14A and 14B respectively, enclosed in a supportive cover 16. Each magnet 14 is preferably disk-shaped and sandwiched between a portion of main body 12 and cover 16. Cover 16 may be affixed to main body 12 by any suitable attachment configuration, such as stitching, adhesive, or welding technique. In an installed configuration, main body 12 saddles the upper rim of regular eyeglasses in generally covering relation with one lens. Apparatus 10 is maintained over the lens by magnetic attraction between magnets 14A and 14B. In the installed configuration, magnets 14 are placed in a proper position in front of the affected eye and their polarity can be changed at any time without any difficulty. Magnets 14 are preferably solid discs of Neodymium-Iron-Boron (NdFeB) with a surface strength of 1300 to 1800 gauss.

Mode of Use

For the treatment of the above mentioned conditions, except for the treatment of glaucoma, the apparatus is placed on the regular glasses with the negative north pole facing the eye for 20-30 minutes once a day for one week, and then reversing the polarity with the south positive pole facing the eye for another week. This alternating treatment is continued for a total of 4 to 6 weeks. For the treatment of glaucoma the treatment consists of 4 to 6 weeks with the negative north pole facing the eye. It is advisable to start the treatment on the more affected eye first in order to observe the results.

Magnets do not have harmful side effects and are exceptionally safe. However persons with pacemakers or other electronic medical devices should be cautious with the use of magnets in a close proximity to these devices. In addition neodymium magnets should be handled with care to avoid damage to magnetic media such as floppy discs, credit cards, magnetic I.D. cards, cassette tapes, video tapes and similar items. They can also damage televisions, VCRs, computer monitors and other CRT electronics. With respect to the use of magnets for treatment of eye conditions there are certain contraindications that should be mentioned here: Neoplasmas in the area to be exposed, retinal detachment, metallic foreign bodies in the eyeball, purulent iridocyclitis and endophtalmitis.

The instant invention has been shown and described herein in what is considered to be the most practical and preferred embodiment. It is recognized, however, that departures may be made therefrom within the scope of the invention and that obvious modifications will occur to a person skilled in the art.

What I claim is:

1. A magnetic apparatus for the treatment of cataracts and other eye conditions for use with conventional eyeglasses having an upper rim and lenses, said magnetic apparatus comprising:
   a main body having a first side and a second side, and a mid-portion disposed between said first and second sides;
   said first side including a first magnet, and said second side including a second magnet;
   said main body sized for removable installation on conventional eyeglasses with said first and second sides disposed on opposing sides of, and in general covering relation with, one of the eyeglass lenses, with said mid-portion disposed in overlapping relation with a portion of the eyeglass upper rim; and
   said main body maintained in place by magnetic attraction between said first and second magnets with said first magnet disposed on a first side of said one of the eyeglass lenses and said second magnet disposed on a second side of said one of the eyeglass lenses with said one of the eyeglass lenses disposed immediately between said first and second magnets.

2. A magnetic apparatus for the treatment of cataracts according to claim 1, wherein said first and second magnets each comprise a solid disk.

3. A magnetic apparatus for the treatment of cataracts according to claim 1, wherein said first and second magnets are each Neodymium-Iron-Boron.

4. A magnetic apparatus for the treatment of cataracts and other eye conditions for use in combination with conventional eyeglasses having an upper rim and lenses, said magnetic apparatus comprising:
   a main body having a top surface, a first side, a second side, and a mid-portion disposed between said first and second sides;
   said first side including a first magnet disposed adjacent to said top surface and a first cover in covering relation with said first magnet;
   said second side including a second magnet disposed adjacent to said top surface and a second cover in covering relation with said second magnet;
   said main body sized for removable installation on conventional eyeglasses with said first and second sides disposed on opposing sides of, and in general covering relation with, one of the eyeglass lenses, with said mid-portion disposed in overlapping relation with a portion of the eyeglass upper rim; and
   said main body maintained in place by magnetic attraction between said first and second magnets exerted through the lens with said first magnet disposed on a first side of said one of the eyeglass lenses and said second magnet disposed on a second side of said one of the eyeglass lenses.

5. A magnetic apparatus for the treatment of cataracts and other eye conditions for use in combination with conventional eyeglasses, said magnetic apparatus comprising:
   a pair of eyeglasses having an upper rim and lenses;
   a main body having a top surface, a first side, a second side, and a mid-portion disposed between said first and second sides;
   said first side including a first magnet disposed adjacent to said top surface and a first cover in covering relation with said first magnet;
   said second side including a second magnet disposed adjacent to said top surface and a second cover in covering relation with said second magnet;
   said first and second magnets comprising solid discs of Neodymium-Iron-Boron having a surface strength of between approximately 1300 to 1800 gauss;
   said main body sized for removable installation on conventional eyeglasses with said first and second sides disposed on opposing sides of, and in general covering relation with, one of the eyeglass lenses, with said mid-portion disposed in overlapping relation with a portion of the eyeglass upper rim; and
   said main body maintained in place by magnetic attraction between said first and second magnets.

* * * * *